United States Patent [19]

Sullivan

[11] Patent Number: 5,067,343

[45] Date of Patent: Nov. 26, 1991

[54] METHOD FOR TESTING WATER IMPERVIOUS CABLE

[75] Inventor: James H. Sullivan, Carrollton, Ga.

[73] Assignee: Southwire Company, Carrollton, Ga.

[21] Appl. No.: 577,190

[22] Filed: Sep. 4, 1990

[51] Int. Cl.⁵ .............................................. G01M 3/22
[52] U.S. Cl. .................................................... 73/40.7
[58] Field of Search .................................. 73/40.7, 40

[56] References Cited

FOREIGN PATENT DOCUMENTS 220710 10/1986 Japan ..................................... 73/40.7

Primary Examiner—Hezron E. Williams
Assistant Examiner—Joseph W. Roskos
Attorney, Agent, or Firm—Stanley L. Tate; James W. Wallis, Jr.

[57] ABSTRACT

A method for testing the water blocking qualities of moisture blocking compound which is applied to the interstitial spaces of a stranded conductor so as to produce a water impervious cable construction, with testing occurring prior to the application of any layers of plastic in the cable's manufacture.

4 Claims, 1 Drawing Sheet

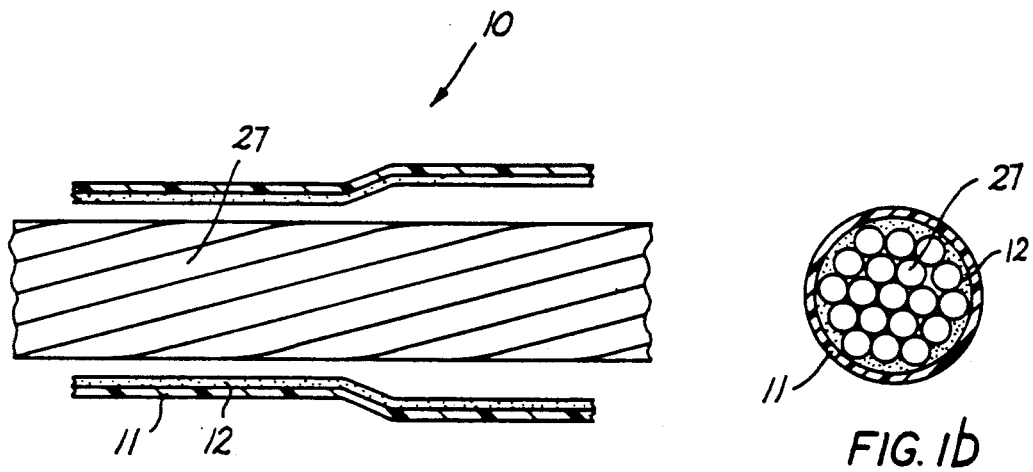
FIG. 1a
FIG. 1b
FIG. 1c
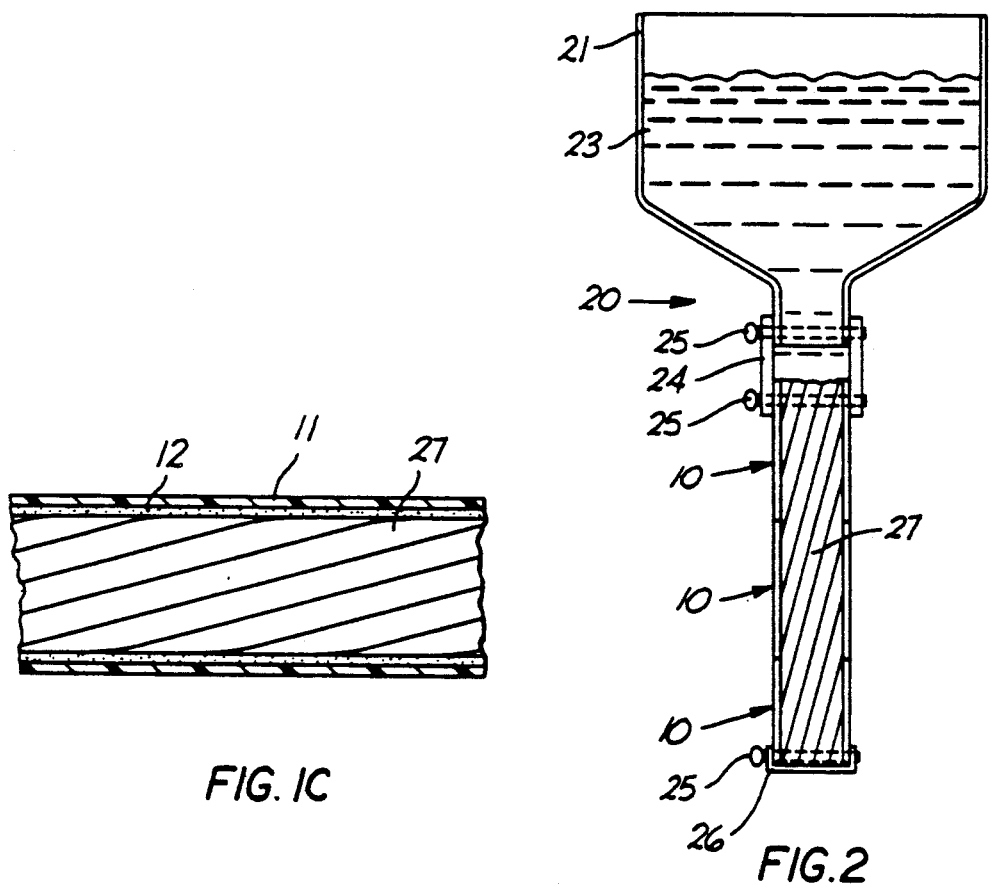
FIG. 2

METHOD FOR TESTING WATER IMPERVIOUS CABLE

TECHNICAL FIELD

This invention relates to an improved method for testing electrical conductors. More particularly, this invention relates to a method for testing the water impervious characteristics of water blocking compound applied to a water impervious cable, during its manufacture, before the cable has been covered with its insulation and jacket layers.

BACKGROUND ART

The manufacture of stranded cable is well known within the wire and cable arts. Taking individual strands of electrical conductor wire and stranding them together provides a cable having a stable configuration and one which is more flexible than a solid conductor capable of carrying the same current load. One of the drawbacks to a stranded cable construction is in its inherent quality of providing a natural passageway for water and moisture to travel the length of the conductor. The interstitial spacings between the strands of conductor wire are natural conduits in which moisture travels. Eliminating this interstitial passageway in which moisture and water travel is known in the industry as "moisture blocking".

The manufacture of stranded moisture blocked electrical cable involves the assembly of a plurality of layers of components. Complex electrical conductor products can comprise multiple layers of stranded conductors encapsulated within multiple layers of special purpose insulation and jacket materials. Moisture blocking these complex constructions includes a material placed within the interstitial spacing of the strands of the conductor which inhibits the flow of moisture within the cable.

The manufacture of complex conductor products is typically accomplished in multiple stages. If the cable construction requires a stranded or bunched configuration, then conductor wires must be supplied to a stranding machine or buncher where they are stranded or bunched. If the construction requires a non-conducting or semi-conducting layer of plastic material in its configuration, this is typically applied in a subsequent step. If intermediate layers of concentric neutral wires are required, they are typically applied in subsequent steps. If a jacket layer is required, it, too, is typically applied in a subsequent step. If the construction calls for moisture blocking characteristics, that is to say, the cable is required to be constructed so as to prevent moisture from flowing longitudinally through the cable, a moisture blocking compound must be applied to the interstitial spaces of the stranded portion of the cable. Such a moisture blocking compound is typically applied to the conductor strands as they are configured or stranded for use within the cable construction. It is the testing of the uniformity and the continuity and effectiveness of the application of this moisture blocking compound which is the subject of the present invention.

The typical procedure for forming a simple water impervious, or moisture blocked cable includes the steps of: providing individual conductor wire strands to a stranding machine; placing water blocking compound on the wires which are to be stranded; stranding the wires which have been coated with the blocking compound; insulating the stranded cable; and placing a jacket over the whole assembly. It should be obvious that the manufacturing procedure of even a simple cable is very complex and very costly. It should also be obvious that if the moisture blocking compound were to be applied improperly, that is to say that it was applied in such a way that it did not block the flow of moisture within the interstitial spaces of the stranded conductor portion of the cable, the cable would be of no use for its intended water resistant application and would have to be scrapped.

Testing the moisture blocking characteristics of the cable is the only way to conclusively determine if it will meet the moisture blocking requirements set out in the specifications for its construction. The current practice in the industry is to test the moisture blocking characteristics of the cable after it is fully constructed. The test essentially comprises the steps of taking a three foot section of the finished cable and securing one end of it to a source of colored water and pressuring the water to between three and five pounds per square inch. The opposite end of the cable is then monitored with some clean, dry, absorbent, white paper which allows the technician performing the test to see if any of the colored water traverses the length of cable. This simple test checks the integrity of the water blocking compound and indicates whether it will function in its intended manner. However, this test has at least one major drawback. It must be performed on a fully and completely manufactured conductor. The stranded conductor wires must be "sealed" within the insulation and jacket before the test can be performed. The pressurized test water is forced down any interstitial spaces of the stranded cable conductor wires which have not been effectively sealed by the moisture blocking compound. The spaces outside of the stranded conductor wires are naturally filled with insulation material so that these spaces are effectively moisture blocked when the plastic is applied. The insulation material keeps the moisture from flowing along the outside of the stranded conductor wires.

These tests are performed on finished cables because if tests of the moisture blocking compound were attempted on uninsulated material, without the stranded conductor being supported by the plastic insulation and jacket layers holding the stranded conductor wires together, the stranded wires would simply disassemble. No test could then be performed because no stranded conductor wire assembly would exist.

Testing the moisture blocking characteristics of the moisture blocking compound applied to the interstitial spacings of the cable, before the construction has been completed, would allow the manufacturer to evaluate the quality of the stranded conductor portion of the cable before the balance of the expensive construction is completed. Such an evaluation could substantially eliminate scrapping completed cable due to improperly applied moisture block compound. The present invention is a method for testing the effectiveness and moisture blocking characteristics of stranded cable conductors after they have been stranded but before they are insulated or jacketed.

DISCLOSURE OF THE INVENTION

It is therefore a primary object of the present invention to provide a method and an apparatus for testing the moisture blocking characteristics of a water impervious cable construction prior to the completion of the construction of such a cable.

It is another object of the present invention to provide a simple test for the integrity of moisture blocking compound which has been placed within the interstitial spaces of a stranded cable.

It is another object of the present invention to provide an indication of the effectiveness of moisture blocking compound which has been applied to the interstitial spaces of a stranded cable before the insulation and jacket layers of said conductor cable have been applied.

It is a primary feature of the present invention that the continuity of a water blocking compound which has been applied to the strands of a stranded conductor, said stranded conductor to be used in a water impervious cable construction, can be evaluated without the need for the cable to be fully constructed.

It is another feature of the present invention that a simple external sheath can be applied to a sample of moisture blocked, stranded conductor which allows same to be tested for moisture blocking properties that it will have after the application of insulation and jacket layers.

Another feature of the present invention is that it is a simple test that can be performed by technicians who require no specialized and skilled training as to the testing procedure.

It is a primary advantage of the present invention that the water blocking characteristics of water blocking compound, which has been applied to the strands of a stranded conductor, can be evaluated before time and money have been expended in completing the construction of such cable.

Another advantage of the present invention is the simplicity of its implementation on a sample of moisture blocked, stranded electrical conductor.

Another advantage of the present invention is the ease by which scrap can be reduced in the manufacture of stranded, moisture blocked cable.

BRIEF DESCRIPTION OF THE DRAWINGS

FIG. 1a is a longitudinal sectional schematic representation of the present invention showing a typical relationship between one of the plurality of heat shrinkable sleeves used to form the outer shell on a sample of stranded conductor.

FIG. 1b is a cross sectional schematic representation of the sleeves as they appear, after they have been heat shrunk, in a cross sectional view of a section of stranded cable which is to be pressure tested.

FIG. 1c is a longitudinal sectional schematic representation of the sleeves as they appear, after they have been heat shrunk, in a longitudinal view of a section of stranded cable which is to be pressure tested.

FIG. 2 is a schematic representation of the present invention showing the relative position of its main components assembled for testing a water blocked stranded conductor.

BEST MODE OF CARRYING OUT THE INVENTION

Refer now to FIG. 1a which is a schematic representation of the spacial relationship between the sleeves used on a sample of the cable and the water blocked conductor. Sleeve 10 comprises a heat activated shrinking outer shell 11 and a lining 12 of glue. When heat is applied to sleeve 10, the outer shell 11 shrinks and takes the form of the cable 27 around which it is positioned. When sleeve 10 is heated, lining 12 becomes soft and shell 11 shrinks. As shell 11 shrinks, it forces the soft glue lining 12 into the outside grooves of stranded conductor 27. Upon cooling, shell 11 then provides a "jacket like" coating on the outside of the conductor cable being tested. The shell provides support and containment for the individual strands which comprise stranded conductor 27. Glue lining 12 provides a seal around the outside of stranded conductor 27 so as to prevent the flow of water around the outside of conductor 27 during the moisture block test.

Refer now to FIG. 1b, which is a cross sectional representation of a sample of water or moisture blocked conductor strand 27 to which has been applied the heat shrink sleeves and which is ready for testing. Conductor strands 27 are held in position by jacket 11 after said jacket has ben heated and shrunk. Glue layer 12 provides a seal around the outside of conductor 27 so as to prevent moisture from flowing along the outside of conductor 27 during the moisture block test.

Refer now to FIG. 1c, which is a longitudinal sectional view of the present invention. Conductor strands 27 are held in position by jacket 11 after said jacket has been heated and shrunk. Glue layer 12 provides a seal around the outside of conductor 27 so as to prevent moisture from flowing along the outside of conductor 27 during the moisture block test.

Refer now to FIG. 2, which is a schematic representation of the present invention showing the relative positions of its main components which have been assembled for testing a water blocked stranded conductor. Test assembly 20 comprises a source 21 of colored liquid 23 which supplies said colored liquid 23 at a pressure of between three and five pounds of pressure per square inch. Attached to source 21 is a connector 24, said connector having an entrance end and an exit end, said entrance end of said connector being secured to source 21 by clamp 25. The action of clamp 25 on connector 24 secures connector 24 to source 21 and forms a water tight seal therebetween.

Secured to said exit end of connector 24 is section of cable 27, said cable having a first and a second end. Said first end of said cable is secured to said connector 24 by clamp 25. An absorbent, light colored, dry material 26 is secured to said second end of cable 27. As pressurized liquid 23 contacts said first end of cable 27, it seeks unblocked interstitial spaces of said stranded cable 27. If unblocked interstitial spaces are present, said colored liquid 23 will traverse the cable 27 along said spaces where it will exit said second end of said cable 27 and will discolor said absorbent, light colored, dry material 26, indicating that said moisture blocking compound was not properly applied and is not effectively blocking cable 27.

What is claimed is:

1. A method for testing the continuity of a water blocking compound, said compound having been applied to the interstitial spacing of a stranded electrical conductor, comprising the steps of:

providing a sample of stranded conductor, said conductor having a first and a second end, said conductor treated with moisture blocking compound;

applying a sealing and supporting means to said stranded conductor for sealing and supporting said stranded conductor strands; connecting said first end of said conductor to a source of colored liquid; and monitoring said second end of said conductor for penetration of said colored liquid.

2. The method according to claim 1, including the additional step of providing said source of liquid to said sample at a pressure of between three and five pounds per square inch.

3. A method for testing the continuity of a water blocking compound, said compound having been applied to the interstitial spacing of a stranded electrical conductor, comprising the steps of:

providing a sample of stranded conductor, said conductor having a first and a second end, said conductor treated with moisture blocking compound;

wrapping said conductor with a glue lined, heat shrink type plastic sheath;

applying sufficient heat such that said sheath shrinks around said stranded conductor sample;

connecting said first end of said conductor to a source of colored liquid; and monitoring said second end of said conductor for penetration of said colored liquid.

4. The method according to claim 3, including the additional step of providing said source of liquid to said sample at a pressure of between three and five pounds per square inch.

* * * * *